US00PP13582P2

(12) United States Plant Patent
Kolster

(10) Patent No.: US PP13,582 P2
(45) Date of Patent: Feb. 18, 2003

(54) ROSE PLANT NAMED 'KOLAMAZ'

(75) Inventor: Peter R. Kolster, Boskoop (NL)

(73) Assignee: Gebr. Kolster B.V., Boskoop (NL)

( * ) Notice: Subject to any disclaimer, the term of this patent is extended or adjusted under 35 U.S.C. 154(b) by 0 days.

(21) Appl. No.: 10/006,842

(22) Filed: Dec. 5, 2001

(51) Int. Cl.[7] ..... A01H 5/00

(52) U.S. Cl. ..... Plt./107

(58) Field of Search ..... Plt./107, 102, 148

(56) References Cited

PUBLICATIONS

UPOV–ROM GTITM Computer Database 2002/03, GTI Jouve Retrieval Software, Citation for Rosa 'Kolamaz'.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Rose plant named 'Kolamaz', characterized by its upright and outwardly spreading plant habit; dark green leaflets; sparse thorns; single purple-colored flowers; orange red-colored fruits; and good post-production longevity.

2 Drawing Sheets

BOTANICAL CLASSIFICATION/CULTIVAR DESIGNATION

*Rosa hybrida* cultivar Kolamaz.

BACKGROUND OF THE INVENTION

The present Invention relates to a new and distinct cultivar of Rose plant, botanically known as *Rosa hybrida,* commercially used as cut stems with fruits or hips, and hereinafter referred to by the name 'Kolamaz'.

The new Rose is a product of a planned breeding program conducted by the Inventor in Boskoop, The Netherlands. The objective of the breeding program was to develop cut Rose varieties with attractive fruit coloration.

The new cultivar originated from a cross made by the Inventor in 1995 of two unidentified proprietary seedling selections, not patented. The cultivar Kolamaz was discovered and selected by the Inventor in 1997 as a flowering plant within the progeny of the stated cross in a controlled environment in Boskoop, The Netherlands.

Asexual reproduction of the new Rose by terminal cuttings taken at Boskoop, The Netherlands, has shown that the unique features of this new Rose are stable and reproduced true to type in successive generations of asexual reproduction.

SUMMARY OF THE INVENTION

The following traits have been repeatedly observed and are determined to be the unique characteristics of 'Kolamaz'. These characteristics in combination distinguish 'Kolamaz' as a new and distinct cultivar:

1. Upright and outwardly spreading plant habit.
2. Dark green leaflets.
3 Sparse thorns.
4. Single purple-colored flowers.
5. Orange red-colored fruits.
6. Good postproduction longevity.

Plants of the new Rose differ from plants of the parent seedling selections primarily in flower and fruit coloration.

Plants of the new Rose can be compared to plants of the Rose cultivar Sensational Fantasy, not patented. In side-by-side comparisons conducted in Boskoop, The Netherlands, plants of the new Rose differed from plants of the cultivar Sensational Fantasy in the following characteristics:

1. Plants of the new Rose were taller than plants of the cultivar Sensational Fantasy.
2. Fruits of plants of the new Rose were more orange in color than fruits of plants of the cultivar Sensational Fantasy.
3. Fruits of plants of the new Rose were more spherical and not as flat as fruits of plants of the cultivar Sensational Fantasy.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph on the first sheet comprises a side perspective view of a typical plant of 'Kolamaz'.

The photographs on the second sheet (top to bottom) are close-up views of a typical upper surface of fully expanded leaves of 'Kolamaz', a typical opened flower of 'Kolamaz', and a typical fruit of 'Kolamaz'.

DETAILED BOTANICAL DESCRIPTION

The new Rose has not been observed under all possible environmental conditions. The phenotype may vary somewhat with variations in environment such as temperature, daylength and light intensity, without, however, any variance in genotype.

The aforementioned photographs, following observations and measurements describe plants grown in Boskoop, The Netherlands, in an outdoor nursery and under commercial production practices. Plants were about three years old. The photographs and description were taken during the summer when outdoor day temperatures ranged from 14 to 27° C. and night temperatures ranged from 7 to 12° C. In the following description, color references are made to The Royal Horticultural Society Colour Chart, 2001 Edition, except where general terms of ordinary dictionary significance are used.

Botanical classification: *Rosa hybrida* cultivar Kolamaz.

Parentage:

*Female parent.*—Unidentified proprietary selection of *Rosa hybrida,* not patented.

*Male parent.*—Unidentified proprietary selection of *Rosa hybrida,* not patented.

Propagation:

*Type.*—Terminal cuttings.

*Time to initiate roots.*—About 40 days at 20° C.

*Time to produce a rooted young plant.*—About 90 days at 20° C.

*Root description.*—Freely branching; medium thickness; brown in color.

Plant description:

*Plant form.*—Upright and outwardly spreading perennial shrub; globular.

*Growth habit.*—Vigorous. Freely branching; dense and bushy growth habit.

*Growth rate.*—During the spring in Boskoop, The Netherlands, plants grow about 20 cm per month.

*Plant height.*—About 1.5 m.

*Plant width* (*spread*).—About 1.5 m.

*Lateral branches.*—Quantity per plant: About 15. Length: About 80 cm. Diameter: About 4 mm. Internode length: About 3.5 cm. Strength: Strong. Texture: Glabrous. Color: 143B. Thorns: Density: Sparse. Shape: Triangular with sharp acuminate apices. Height: About 4 mm. Diameter, at base: About 5 mm. Color: 175A.

*Foliage description.*—Leaves alternate; compound with five to seven leaflets. Quantity per lateral branch: About 18. Leaf length: About 8.5 cm. Leaf width: About 6 cm. Leaflet length: About 3.3 cm. Leaflet width: About 2 cm. Leaflet shape: Elliptic. Leaflet apex: Acute. Leaflet base: Rounded to attenuate. Leaflet margin: Serrate. Leaflet texture, upper and lower surfaces: Glabrous; smooth. Leaflet venation pattern: Pinnate. Leaflet color: Developing leaflets, upper surface: 143A. Developing leaflets, lower surface: 143C. Fully expanded leaflets, upper surface: 139A. Fully expanded leaflets, lower surface: 137C. Venation, upper surface: 139A. Venation, lower surface: 144C. Leaf petiole: Length: About 2.5 cm. Diameter: About 1 mm. Texture, upper and lower surfaces: Smooth, glabrous. Leaf rachis texture: Smooth. Color, upper and lower surfaces: 144C. Stipules: Quantity per leaf: Two. Arrangement: One stipule on either side of the leaf petiole. Shape: Lanceolate. Length: About 2.5 cm. Diameter: Less than 1 cm. Color: Upper surface: 137A. Lower surface: 138A.

Flower description:

*Flower type and habit.*—Purple single flowers arranged in compound corymbs with about 50 flowers and flower buds per corymb. Flowers flat and rotate. Flowers not persistent. Flowers face mostly upright or outward.

*Natural flowering season.*—Summer, typically July and August in Boskoop, The Netherlands; flowering period lasts about nine weeks; flowering continuous during this period.

*Postproduction longevity.*—Cut stems are typically harvested when all flowers have developed fruits. Flowers typically last a few days. Postproduction longevity of cut stems with fruits is more than two weeks.

*Fragrance.*—Strong, typical of Rosa, sweet.

*Inflorescence height.*—About 15 cm.

*Inflorescence diameter.*—About 20 cm.

*Flower buds.*—Height: About 3 mm. Diameter: About 0.8 mm. Shape: Narrowly ovoid. Color: 143A to 143B.

*Flowers.*—Diameter: About 5.5 cm. Depth: About 1 cm.

*Petals.*—Quantity per flower: Five. Length: About 2.5 cm. Width: About 3 cm. Shape: Obcordate. Aspect: Slightly reflexed. Apex: Retuse. Base: Attenuate. Margin: Entire. Texture, upper and lower surfaces: Smooth. Color: Developing and fully expanded petals, upper surface: 70B; towards the base, lighter than 70B; color does not fade with subsequent development. Developing and fully expanded petals, lower surface: 75B.

*Sepals.*—Quantity per flower: Five. Length: About 2.5 cm. Width: About 4 mm. Shape: Narrowly lanceolate. Aspect: Flat. Apex: Acute. Base: Broadly cuneate. Margin: Entire. Texture: Upper surface: Smooth. Lower surface: Covered with numerous stalked glands. Glands, about 0.3 mm in length and dark brown to almost black in color. Stalks, greenish white in color. Color: Developing and fully expanded sepals, upper surface: 138B. Developing and fully expanded sepals, lower surface: 143A to 143B.

*Peduncles.*—Length: About 8 cm. Diameter: About 2 mm. Orientation: About 30 to 50° from vertical. Strength: Strong. Color: 143B.

*Pedicels.*—Length: About 2 cm. Diameter: About 1.2 mm. Orientation: Erect to about 50° from vertical. Strength: Strong. Color: 143B.

*Reproductive organs.*—Stamens: Quantity per flower: About 100. Anther shape: Reniform, irregular. Anther length: About 1.2 mm. Anther color: 13A. Pollen amount: Abundant. Pollen color: 8B. Pistils: Quantity per flower: About 30. Pistil length: About 0.5 mm. Stigma shape: Oval, flattened. Stigma color: 145A to 145B. Style length: Less than 0.5 mm; minute. Ovary color: 143A to 143B.

*Fruits.*—Quantity per flower: One. Days to ripening: About 40. Type: Fleshy hip. Shape: Roughly spherical. Length: About 1.5 cm. Diameter: About 1.6 cm. Texture: Smooth, glabrous. Color: 28A to N30D, overlain with N30A; glossy.

*Seeds.*—Quantity per fruit: About 35. Length: About 4 mm. Diameter: About 2 mm. Color: 162A to 162B.

Disease susceptibility: Plants of the new Rose have been observed to not be susceptible to pathogens common to Rose, such as mildew and Black Spot.

Temperature tolerance: Plants of the new Rose have been observed to tolerate temperatures ranging from −30 to 35° C.

It is claimed:

1. A new and distinct cultivar of Rose plant named 'Kolamaz', as illustrated and described.

* * * * *

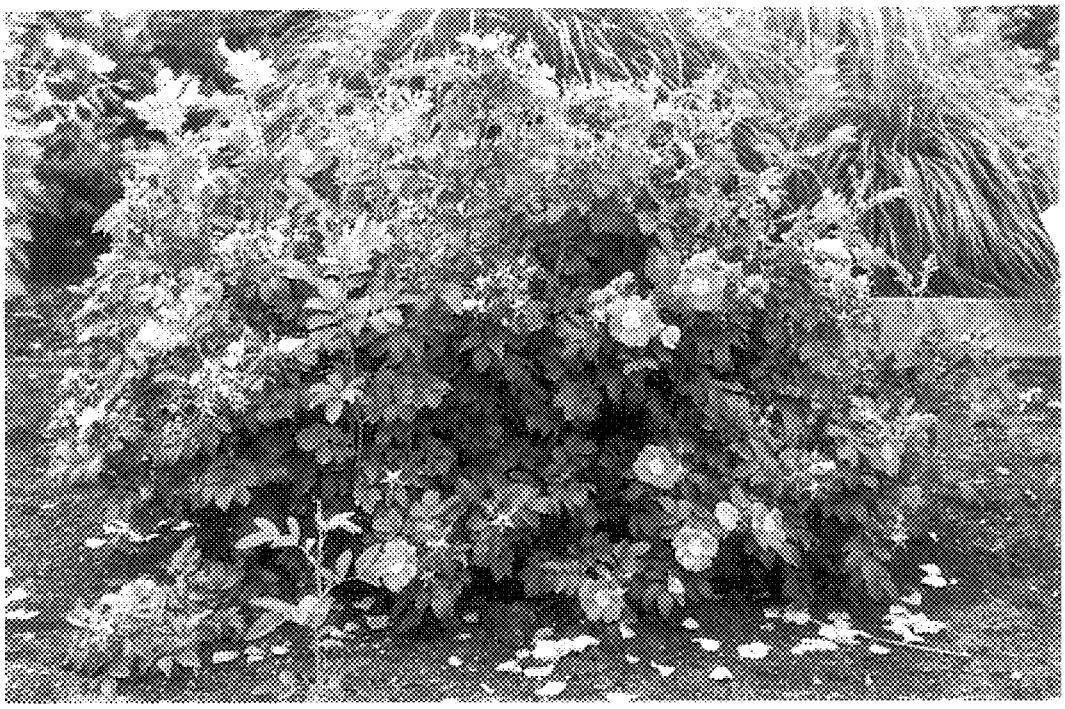

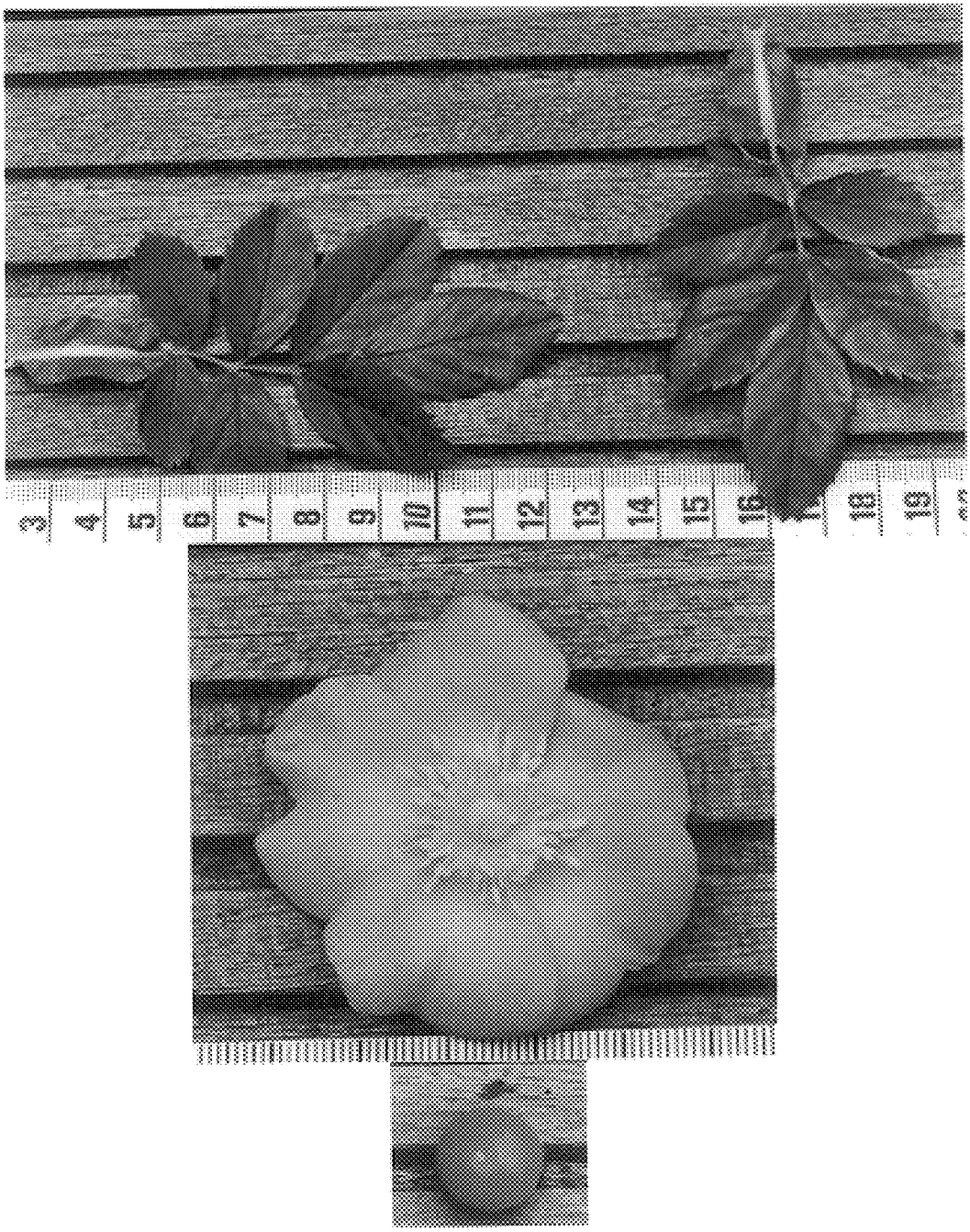
3
4
5
6
7
8
9
10
11
12
13
14
15
16
18
19